United States Patent [19]
Fassihi et al.

[11] Patent Number: 5,783,212
[45] Date of Patent: Jul. 21, 1998

[54] CONTROLLED RELEASE DRUG DELIVERY SYSTEM

[75] Inventors: Reza Fassihi, Ambler; Libo Yang, Philadelphia, both of Pa.

[73] Assignee: Temple University—of the Commonwealth System of Higher Education, Philadelphia, Pa.

[21] Appl. No.: 595,660

[22] Filed: Feb. 2, 1996

[51] Int. Cl.$^6$ .............................. A61K 9/32; A61K 9/20; A61K 9/30

[52] U.S. Cl. ......................... 424/472; 424/464; 424/468; 424/471; 424/475; 424/482

[58] Field of Search ................................... 424/472, 468, 424/471, 475, 482

[56] References Cited

U.S. PATENT DOCUMENTS

| | | | |
|---|---|---|---|
| 3,113,076 | 12/1963 | Jacobs | 167/82 |
| 4,681,755 | 7/1987 | Colombo et al. | 424/486 |
| 4,744,976 | 5/1988 | Snipes et al. | 424/408 |
| 4,792,452 | 12/1988 | Howard et al. | 424/475 |
| 4,803,081 | 2/1989 | Falk et al. | 424/488 |
| 4,839,177 | 6/1989 | Colombo et al. | 424/482 |
| 4,844,901 | 7/1989 | Leslie et al. | 424/494 |
| 4,865,849 | 9/1989 | Conte et al. | 424/494 |
| 4,942,040 | 7/1990 | Ragnarsson et al. | 424/486 |
| 5,051,263 | 9/1991 | Barry et al. | 424/490 |
| 5,273,760 | 12/1993 | Oshlack et al. | 424/480 |
| 5,393,765 | 2/1995 | Infeld et al. | 514/365 |
| 5,395,626 | 3/1995 | Kotwal et al. | 424/472 |
| 5,626,874 | 5/1997 | Conte et al. | 424/464 |

FOREIGN PATENT DOCUMENTS

| | | |
|---|---|---|
| 0 316 838 | 5/1989 | European Pat. Off. . |
| 0 432 607 | 6/1991 | European Pat. Off. . |
| 0 598 309 | 5/1994 | European Pat. Off. . |

OTHER PUBLICATIONS

U. Conte, L. Maggi, and A. La Manna, "Geomatrix® Technology for the Extended Release of Drugs At a Constant Rate," *Proceed. Intern. Symp. Control Rel. Bioact. Mater.* 20(1993), Controlled Release Society, Inc., pp. 350–351.

U. Conte, L. Maggi, and A. La Manna, "A Multi–Layered Matrix Tablet Design for Constant Drug Release," *Proceed. Intern. Symp. Control. Re. Bioact. Mater.*, 19(1992), Control Release Society, Inc., pp. 369–370.

R. A. Fassihi and W. A. Ritschel, "Multiple–Layer, Direct–Compression, Controlled–Release System: In Vitro and In Vivo Evaluation," *Journal of Pharmaceutical Sciences*, vol. 82, No. 7, Jul. 1993, pp. 750–754.

A. G. Hansson, A. Giardino, J. R. Cardinal, and W. Curatolo, "Perforated Coated Tablets for Controlled Release of Drugs at a Constant Rate," *Journal of Pharmaceutical Sciences*, vol. 77, No. 4, Apr. 1988, pp. 322–324.

G. W. Sinclair and N. A. Peppas, "Analysis of Non-fickian Transport in Polymers Using Simplified Exponential Expressions," *Journal of Membrane Science*, 17(1984), pp. 329–331.

P. S. Banerjee and J. R. Robinson, "Novel Drug Delivery Systems—An Overview of Their Impact on Clinical Pharmacokinetic Studies," *Clinical Pharmacokinet.* 20(1), 1991, pp. 1–14.

P. Colombo, P. L. Catellani, N. A. Peppas, L. Maggi, and U. Conte, "Swelling Characteristics of Hydrophilic Matrices for Controlled Release. New Dimensionless Number to Describe the Swelling and Release Behavior," *International Journal of Pharmaceutics*, 88(1992), pp. 99–109.

P. Colombo, "Swelling–Controlled Release in Hydrogel Matrices for Oral Route," *Advanced Drug Delivery Reviews*, 11 (1993), pp. 37–57.

U. Conte, L. Maggi, and A. La Manna, "Compressed Barrier Layers for Constant Drug Release from Swellable Matrix Tablets," *S.T.P. Pharma Sciences*, 4 (2), 1994, pp. 107–113.

A. R. Fassihi, "In–Vitro and In–Vivo Evaluation of a Controlled Release Preparation of Theophylline", *Journal of Pharmacy and Pharmacology*, 1988, vol. 40, p. 32P.

J. Timmermans and A. J. Moës, "Factors Controlling the Buoyancy and Gastric Retention Capabilities of Floating Matrix Capsules: New Data for Reconsidering the Controversy," *Journal of Pharmaceutical Sciences*, vol. 83, No. 1, Jan. 1994, pp. 18–24.

H. M. Ingani, J. Timmermans and A. J. Moës, "Conception and In Vivo Investigation of Peroral Sustained Release Floating Dosage Forms with Enhanced Gastrointestinal Transit," *International Journal of Pharmaceutics*, 35(1987), pp. 157–164.

S. Desai and S. Bolton, "A Floating Controlled–Release Drug Delivery System: In Vitro–in Vivo Evaluation," *Pharmaceutical Research*, vol. 10, No. 9, 1993, pp. 1321–1325.

M. R. Jiménez–Castellanos, H. Zia, and C. T. Rhodes, "Design and Testing In Vitro of a Bioadhesive and Floating Drug Delivery System for Oral Application," *International Journal of Pharmaceutics*, 105 (1994), pp. 65–70.

U. Conte, L. Maggi, P. Colombo, and A. La Manna, "Multi–Layered Hydrophilic Matrices as Constant Release Devices (Geomatrix™ Systems)," *Journal of Controlled Release*, 26 (1993), pp. 39–47.

L. Krowczynski, "Extended Release Dosage Forms," CRC Press, Boca Raton, FL, 1987, pp. 145–146.

*Primary Examiner*—Fred Zitomer
*Attorney, Agent, or Firm*—Ratner & Prestia

[57] ABSTRACT

The present invention pertains to a controlled release pharmaceutical tablet having at least three layers, two barrier layers and one drug layer. The two barrier layers erode more quickly than the drug layer. All layers are formed from swellable, erodible polymers. The drug layer can have a different composition from the two barrier layers. The three layers can also differ in thickness. The pharmaceutical agent is contained in the drug layer and is released as the tablet layer swells to allow diffusion through the tablet layers, and as the layers erode. The barrier layers are made from swellable erodible polymers which erode away to reveal more of the drug layer, as the tablet dissolves.

29 Claims, 9 Drawing Sheets

CONTROLLED RELEASE DRUG DELIVERY SYSTEM

FIELD OF THE INVENTION

This invention is directed to a multi-layered controlled release pharmaceutical dosage form. More particularly, the dosage form is adapted for controlled release of various pharmaceuticals and comprises a multi-layered tablet.

BACKGROUND OF THE INVENTION

Controlled release pharmaceutical dosage forms have received much attention lately. Such controlled release tablets are highly desirable for providing a constant level of pharmaceutical agent to a patient. Attempts at controlled release tablets have been made in the past, with mixed success. One of the main problems with such tablets is that the rate of release of pharmaceutical agents from the tablets is generally proportional to the surface area of the tablet. As the tablet shrinks, so does the rate of pharmaceutical release. There are various ways of overcoming this, including the choice of drug and excipient so that there is an interaction which delays release of the pharmaceutical agent during the earlier stages, leading to a more constant drug release. Of course, a system whereby the surface area of the tablet would remain nearly constant throughout dissolution of the tablet would be most likely to achieve zero-order drug release with a multitude of drugs, but such a system has heretofore been difficult to envision.

Various approaches exist for the preparation of controlled release dosage forms. One commonly known technique is to form a matrix by entrapping the drug in excipients. Diffusion and/or erosion operate to release the active drug substance depending on the properties of the drug and the polymer incorporated in the formulation. As previously stated, the amount of drug available at the absorption site (the surface area) decreases with time, which is the major drawback of these dosage forms. In zero-order release, the amount of drug release remains constant with respect to time. Prior methods for preparing zero-order controlled release dosage forms include those operating by a rate controlling membrane and by osmotic pumps.

One particular attempt at controlled release is detailed in European Patent publication 0 593 309 A2 to Columbo. The publication shows a three-layer system consisting of two external swelling layers separated by an interposed soluble layer, and a two-layer system consisting of a swellable layer adjacent a soluble and/or erodible layer. The swellable layer(s) consist of methyl cellulose, carboxymethylcellulose sodium, crosslinked carboxymethylcellulose sodium, crosslinked hydroxypropylcellulose, hydroxypropylmethylcellulose, carboxymethyl starch, polymethacrylate, polyvinylpyrrolidone, polyvinyl alcohols, polyethylene glycols, or potassium methacrylate-divinyl benzene copolymer and mixtures thereof. However, the swellable materials used are not erodible.

The soluble and/or erodible layer consists of hydroxyethylcellulose, carboxymethylcellulose, alginates, albumin, soluble starch and gelatin, mixed with soluble excipients such as saccharides and polyalcohols. The swellable layer(s) contain an active pharmaceutical agent. As the swellable layers swell and the erodible layer erodes, the pharmaceutical agent is released from the swellable layers. However, the resulting rate of pharmaceutical release is not zero-order. The swellable layers including pharmaceutical agent sandwich the erodible pharmaceutical-free layer. Thus, as the erodible layer dissolves, more of the swellable layers are revealed. However, the erodible layer is not swellable. Rather it erodes. Since the erodible layer does not swell, no pharmaceutical can escape through the erodible layer. The erodible layer must erode to expose swellable layer and allow pharmaceutical agent to be released. While the erosion of the erodible layer reveals swellable layer, increasing the surface area through which water may diffuse into the swellable layer and the pharmaceutical agent may diffuse out of the swellable layer, the increase is not great enough to provide a zero-order result. Further, the swellable, non-erodible polymer masses must pass through the patient intact. Recently regulatory concerns have been raised concerning the possibility of such swollen masses causing blockages in a patient. Thus the need for a zero-order release tablet without these drawbacks still exists.

SUMMARY OF THE INVENTION

The present invention pertains to a multi-layered tablet having at least three layers and an active pharmaceutical agent in at least one layer, referred to as the drug layer. The three layers are formed from swellable, erodible polymers. The tablet may be asymmetric in that the three layers may have different rates of swelling and/or erosion, or different thicknesses. The barrier layers erode more quickly than the drug-containing layer. As the barrier layers swell, water can diffuse into the drug layer and pharmaceutical agent can diffuse out of the drug layer, through the swollen barrier layers. The drug is thus released. As the swollen barrier layer erodes away, the rate of diffusion of the drug through the layer increases, until no swollen barrier layer remains. At this time, the drug diffuses directly out of the drug layer. Thus as the tablet dissolves and shrinks, more pharmaceutical agent can be released through the swollen barrier layers, compensating for the decrease in surface area of the pharmaceutical-containing layer, and achieving zero-order release.

DETAILED DESCRIPTION OF THE INVENTION

The present invention provides a zero-order controlled release drug delivery system including at least three swellable layers, at least one of which includes a pharmaceutical agent. The tablet of the present invention is shown in FIG. 1.

Figure 1:
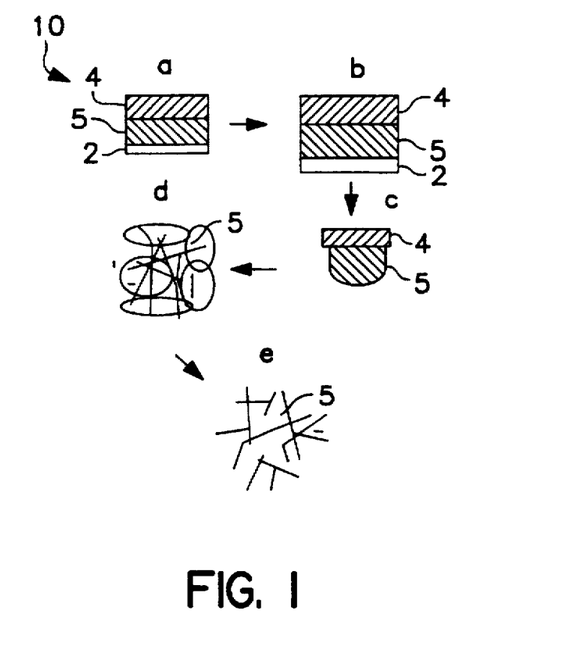
FIG. 1 is a representation of the stages of dissolution of the tablet of the present invention.

FIG. 1 shows a three layer asymmetric controlled release tablet 10 of the present invention. Tablet 10 comprises three layers, a first barrier layer 2, a second barrier layer 4, and drug layer 5. This intact tablet is shown in FIG. 1A. Although the tablet shown in FIG. 1 includes two barrier layers, the tablet could include additional drug or barrier layers (or four or more layers total). Once the tablet is placed in an aqueous medium, or ingested by a patient, the tablet begins to swell as shown in FIG. 1B. All of the layers, drug layer 5 as well as barrier layers 2 and 4, of tablet 10 swell. Drug layer 5 of tablet 10 contains an active pharmaceutical agent.

As tablet 10 is placed in water, or other appropriate aqueous medium, initially the pharmaceutical agent is trapped in dry, solid, drug layer 5. The drug can diffuse out of drug layer 5 only around the circumference of the tablet, as aqueous medium begins to penetrate the circumference. As drug layer 5 and barrier layers 2 and 4 being to swell as shown in FIG. 1B, drug begins to diffuse not only through the circumference of drug layer 5, but also through barrier layers 2 and 4. Barrier layers 2 and 4 are swellable layers. Once these layers swell, diffusion can take place through the swollen polymer. Diffusion takes place both into and out of the tablet. That is, water diffuses into the tablet, through barrier layers 2 and 4, and pharmaceutical agent diffuses out of the tablet, also through barrier layers 2 and 4. Barrier layers 2 and 4 are generally free of pharmaceutical agents. However it should be noted that one or both of barrier layers 2 and 4 can include a pharmaceutical agent if such is desired.

The barrier layers 2 and 4 and the drug layer 5 are designed to have different dissolution or erosion rates. Preferably, all three layers comprising tablet 10 are designed to have different dissolution or erosion rates. All layers are prepared from polymers which, once hydrated, will erode completely. Such polymers, once ingested by a human, or introduced into an aqueous medium, will absorb water and swell. Once swollen, these erodible polymers will erode due to mechanical action. Such erosion is controlled both by the molecular weight of the polymer selected and by the excipients with which it may be mixed. Specifically, a lower molecular weight polymer will erode faster than a higher molecular weight polymer, if both are pure.

Erosion promoters, such as lactose, may be added to either polymer to increase the rate of erosion. Thus a higher molecular weight polymer with an erosion promoter may erode faster than a lower molecular weight polymer with less or no erosion promoter. Further, if the molecular weights of polymers, and the proportion of erosion promoters, are the same for any two layers, the thinner layer will erode away first. In FIG. 1, barrier layer 2 erodes away fastest (as it is the thinnest layer), followed by barrier layer 4 and drug layer 5. Barrier layer 2 and barrier layer 4 may be prepared from the same or different polymers.

The erosion of barrier layer 2 can be seen from FIG. 1C, where barrier layer 2 has eroded away, but barrier layer 4 is swollen and partially eroded, but in place. As previously stated, once barrier layers 2 and 4 swell, they become water permeable. The more they swell, the more water permeable they become. Water can thus penetrate to drug layer 5 and drug can diffuse out of drug layer 5 through barrier layers 2 and 4. As time passes, barrier layers 2 and 4 swell further. Then, through erosion, barrier layers 2 and 4 thin, eventually eroding away completely, beginning with barrier layer 2.

This increases the surface area of drug layer 5 and allows even more drug to be released than when barrier layer 2 remained intact, although highly swollen and thin. Again, as drug layer 5 shrinks further and thus the surface area of drug layer 5 decreases, barrier layer 4 thins as it erodes away, thus allowing more penetration of water and diffusion of drug through barrier layer 4. In FIG. 1D, barrier layers 2 and 4 have eroded away completely and drug layer 5 has swollen to produce a highly hydrated swollen, loose polymer matrix. This matrix dissolves and erodes away. A lower density, more fully eroded matrix is shown in FIG. 1E, and thereafter, the matrix erodes completely.

Optionally, pharmaceutical agent can be added to either one or both of the two barrier layers. Specifically, adding pharmaceutical agent to faster-eroding barrier layer 2 would introduce pharmaceutical agent more quickly at first, followed by controlled release of further pharmaceutical agent, or of a second pharmaceutical agent from drug layer 5. This can be effective when a high concentration of drug is needed to be administered quickly to alleviate symptoms, followed by low levels of drug released to maintain an acceptable pharmaceutical level in the patient. Further, the pharmaceutical agent in the barrier layer can differ from that in drug layer 5.

Any layer can also include a gas evolving material. The gas evolving material is used to evolve gas which will cause the tablet to float, and increase the time of retention of the tablet in the patient's stomach. This prevents premature passage of the tablet into the small intestine. This is especially important for drugs which are particularly effective from the stomach or such acidic environment. The gas evolving material can be any conventional gas evolving system. Specifically, sodium bicarbonate can be used, either alone or with citric acid. The citric acid will react with sodium bicarbonate to produce gas. However, it is generally unnecessary to add citric acid since stomach acid will also react with the sodium bicarbonate to produce gas. Since the sodium bicarbonate is intimately mixed with the swellable polymer, the gas evolved is held within the swollen polymeric matrix, inflating the matrix and ensuring floatation of the tablet.

If floatation is not desired, the sodium bicarbonate should be omitted. Instead of sodium bicarbonate (or in addition thereto) a layer can include calcium carbonate and citric acid as a gas-evolving material. It is generally necessary to include citric acid with calcium carbonate to get acceptable gas evolution. Further, both sodium and calcium carbonates can be used together, with citric acid. Finally, if floatation is desired, the gas evolving material should be incorporated into at least one of the two outer layers because initially, the drug layer is exposed to the dissolution medium only at the edge of the tablet. Thus this layer is slow to swell and would be slow to evolve gas.

The proportions of the different components which may be used in the tablet layers are shown in Table 1.

TABLE 1

Formulation Components of Asymmetric Configuration Drug Delivery System

| Layer | Components | % (w/w) |
|---|---|---|
| 4 | Swellable Polymer | 30–90 |
|  | Gas Evolving Material | 0–40 |
|  | Erosion Promoting Material | 0–70 |
|  | Pharmaceutical Agent | 0–40 |

TABLE 1-continued

Formulation Components of Asymmetric Configuration Drug Delivery System

| Layer | Components | % (w/w) |
|---|---|---|
| 5 | Swellable Polymer | 30–90 |
| | Pharmaceutically Active Agent | 20–40 |
| | Erosion Promoting Material | 0–70 |
| | Gas Evolving Material | 0–40 |
| 2 | Swellable Polymer | 30–90 |
| | Gas Evolving Material | 0–40 |
| | Erosion Promoting Material | 0–70 |
| | Pharmaceutical Agent | 0–40 |

The relative percentages of the various components will change with the desired release rate and compression used to produce the tablet. In each case, the layer includes "Swellable Polymer." The tablet can be formulated using any suitable swellable polymer, including, but not limited to, polyethylene oxide (PEO), hydroxypropylmethylcellulose (HPMC), carboxymethylcellulose (CMC), or combinations thereof. The weight percent shown for the swellable polymer reflects the total weight of PEO, HPMC, CMC, other swellable polymer, or combinations thereof. Each layer may also include lactose or a suitable substitute erosion promoter. Any or all layers may include any further suitable conventional excipients such as magnesium stearate, talc, silica, etc.

The choice and amount of swellable polymer is important to the proper functioning of the invention. The polymers for the drug and barrier layers should be selected such that the barrier layer will erode away before the drug layer. Therefore it is desirable to select a polymer for the barrier layers having a lower molecular weight than that selected for the drug layer. Since a lower molecular weight polymer will erode faster than a higher molecular weight polymer, the higher molecular weight polymer should be used for the drug layer. However, as previously stated, a suitable material may be added to promote erosion of the polymer. That material could be lactose, mannitol, or other polyalcohols, as is known in the art. Thus a higher molecular weight polymer used in a lower amount, and having a greater proportion of lactose may erode faster than a lower molecular weight polymer having a lower proportion of lactose. In such a case, the higher molecular weight polymer which erodes faster should be used for the barrier layer and the slower eroding lower molecular weight polymer should be used for the drug layer. This combination is unusual, but may be desirable in some circumstances. Generally, the higher molecular weight polymer will be used for the drug layer and the lower molecular weight polymer will be used for the barrier layer. Where PEO is used as the swellable polymer, the PEO selected should have an average molecular weight between $8 \times 10^5$ and $8 \times 10^6$. Most preferably, the PEO will have a molecular weight between $1 \times 10^6$ and $2 \times 10^6$.

The rate of swelling and erosion varies with the molecular weight of the polymer and the amount of erosion promoter added. Further, the actual time for erosion of a layer is affected by the thickness of the layer. Finally, the molecular weight of the polymer also affects the diffusivity of the swollen layer. Thus, when designing a zero-order tablet, the molecular weight of the polymer as well as the thickness of the barrier layer must be adjusted to provide the appropriate swelling rate and diffusivity. Once this is determined, the erosion rate can be increased with appropriate increases in the proportion of erosion promoter used (such as lactose, mannitol, etc.).

Drug layer 5 includes a pharmaceutically active agent. That agent (or drug) can be any one of many agents. It is not necessary that the drug be water soluble or insoluble, since the invention is centered around controlling the surface area of drug layer 5, which is exposed to the medium either directly or via diffusion through one or both of the barrier layers. Specifically, and without limitation, pharmaceuticals with which the present invention are useful include nifedipine, theophylline, diltiazem, and diclofenac.

Although the description of the invention has focused on three-layered tablets, the invention contemplates tablets with four, five, or even more layers. It might be desirable to add a second drug layer, for instance, or a further barrier layer. Such arrangements are limited practically by the requirement that the size of the tablet, as well as the cost of manufacturing, must be kept within acceptable ranges.

Experimental Results

Polyethylene oxides of average molecular weight $1 \times 10^6$ and $7 \times 10^6$ were obtained from Union Carbide Corp. of Danbury, Conn. as Polyox/WSR NF. Hydroxylpropylmethylcellulose (HPMC) was obtained from the Dow Chemical Company of Midland, Michigan as Methocel K4M. Theophylline anhydrous USP and magnesium stearate were purchased from Amend Company of Irving, N.J. Other excipients were all of USP or NF grades.

EXAMPLE 1

The formulations shown in Table 2 were mixed after screening the powders through a No. 20 U.S. standard sieve. The mixing was performed in a cube mixer for 15 minutes. Tablets were manufactured using a Carver laboratory press (Model C from Fred S. Carver, Inc. of Wabash, Ind.). The tablets were manufactured using a 10 mm diameter flat faced punch and a die. The material was introduced into the die manually, one layer at a time, compressing after each layer. The first and second layers were initially compressed to 900 lb. and, after addition of the third layer, the entire tablet was compressed to the desired compression force (where unspecified, 2500 lb.).

TABLE 2

| Composition | Amount (%) | Amount (mg) |
|---|---|---|
| First Layer (4) | | |
| Calcium carbonate | 20% | 40 |
| Sodium bicarbonate | 10% | 20 |
| Citric acid | 2% | 4 |
| HPMC K4M | 10% | 20 |
| Polyethylene oxide (MW 7000000) | 58% | 116 |
| | | 200 |
| Second Layer (5) | | |
| Theophylline anhydrous | 33.3% | 100 |
| Polyethylene oxide (MW 1000000) | 54% | 162 |
| Lactose anhydrous | 11.7% | 35 |
| Magnesium stearate | 1% | 3 |
| | | 300 |
| Third Layer (2) | | |
| Lactose anhydrous | 50% | 15 |
| Polyethylene oxide (MW 1000000) | 45% | 13.5 |
| Sodium bicarbonate | 4% | 1.2 |
| Magnesium stearate | 1% | 0.3 |
| | | 30 |

Note: Total weight of the tablet examined = 530 mg

The completed tablets were tested by placing the tablet in a dissolution medium consisting of 0.1N HCl solution. The solution was stirred at 50 rpm and maintained at 37° C. In this set of experiments, anhydrous theophylline was chosen as a drug model. The amount of theophylline released at each test point was measured by a Hewlett Packard HP8451A diode array spectrophotometer at 272 nanometers.

For each tablet, a buoyancy lag time was determined. This was accomplished by measuring the time interval between the introduction of the tablet into the dissolution medium and its ascent to the upper ⅓ of the dissolution vessel. The tablets then floated for the remainder of the test, until dissolution was complete.

The matrix erosion and dissolution was measured by removing individual tablets from the dissolution medium at preselected time intervals and placing the tablets on tin foil in a dryer at 60° C. under vacuum. Once a constant weight was received, the weight loss corresponding to the amount of drug dissolved and fraction eroded was calculated.

The hydrophilic polymer employed in tablets such as those of the present invention is often considered to be of great importance, as drug release is thought to be controlled by diffusion of water into the matrix, and drug diffusion out of the matrix, along with erosion of the polymer matrix. Generally, overall release kinetics depend on the relative rates of polymer swelling and polymer erosion. Where the polymer swells at the same rate the polymer erodes, linear release kinetics are obtained. The fraction of drug released can be expressed as a power function of time where the fraction of drug released equals $K \cdot T^n$. In this equation, K is a constant depending on the characteristics of the system, and n describes the operating release mechanism. Where n=0.5, drug release follows fickian transport mechanism, while where n>0.5, anomalous diffusion occurs, and when N=1, zero-order kinetics prevail.

The use of PEO in controlled release tablets is known. It appears that higher molecular weight PEO (MW>$2\times10^6$, and especially >$4\times10^6$) mainly undergoes relaxation during the dissolution process and drug release is governed by the swelling of the polymer rather than the erosion of the polymer. In contrast, low molecular weight PEO (MW≤$1\times10^6$) exhibits both swelling and erosion characteristics. Drug release in low molecular weight PEO is controlled predominantly by the swelling/erosion of the polymer, which aids in achieving linear release, as long as the surface area of the tablet is kept constant. This is quite difficult. Attempts to achieve constant surface area tablets have most often failed in the past. However, the present invention achieves the goal of zero-order release by controlling the surface area of the drug-containing layer.

Figure 2:
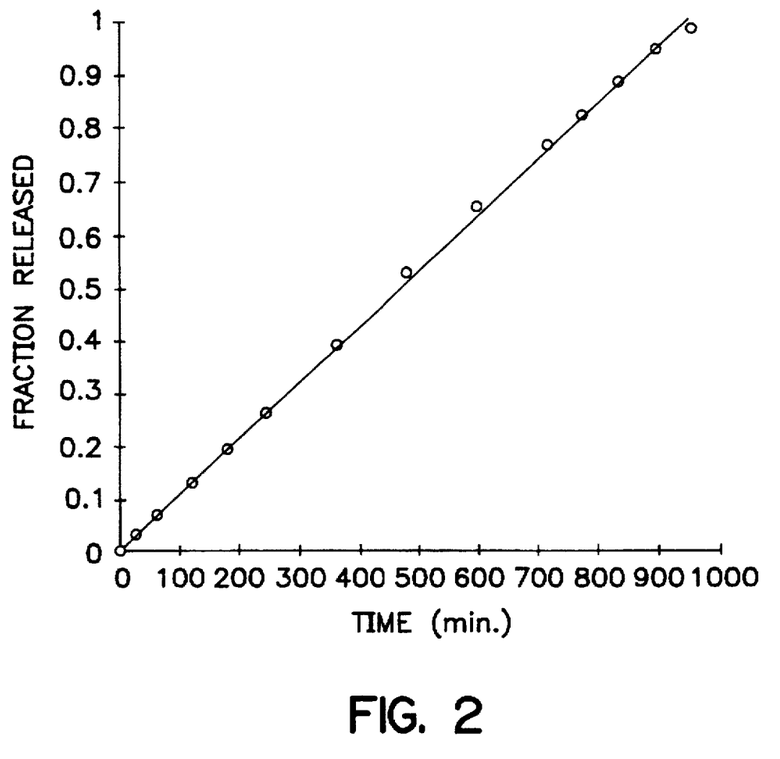
FIG. 2 is a graph showing the fraction of theophylline released versus time using the tablet of example 1 of the present invention.

FIG. 2 shows the fraction of theophylline released versus time. As can be seen from FIG. 2, the theophylline release from the tablets made according to the present invention was nearly constant in a 0.1N HCl solution over a 16 hour period. Thus, the fraction of drug released equals K×T (n=1).

Figure 3:
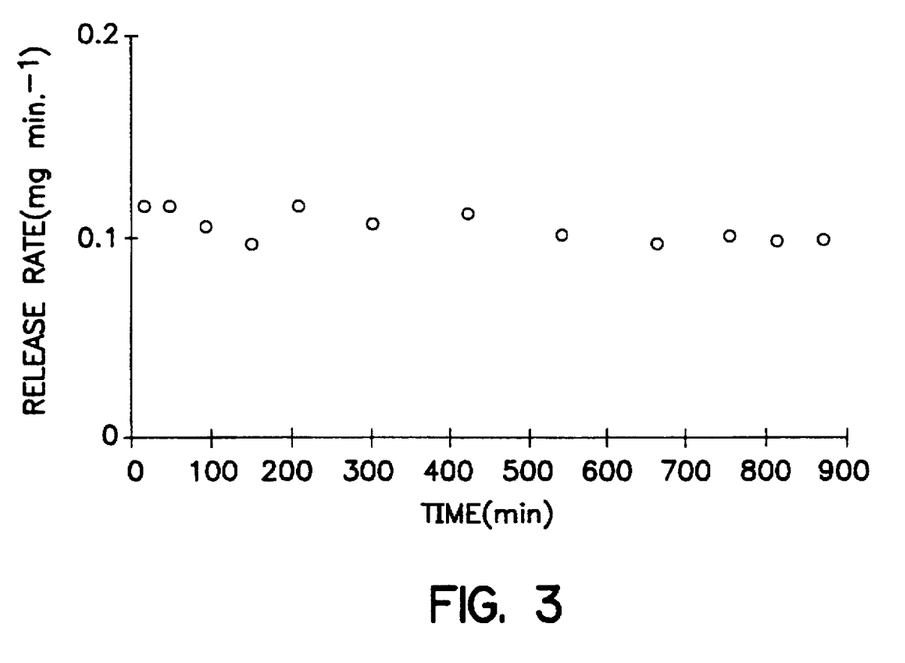
FIG. 3 is a graph of the release rate of theophylline versus time from the tablet of example 1 of the present invention.

FIG. 3 shows the rate of release of theophylline in mg/min. at various times during the 16 hour experiment. As shown in FIG. 3, the release rate of theophylline remains around 0.1 mg/min. throughout the release study. The difference in release rate between the first calculated time point (0.115 mg/min.) and the last point (0.097 mg/min.) is only about 0.018 mg/min. This represents a variation of no more than 16% over 16 hours, for extremes of release times. Such release kinetics are virtually zero-order and highly desirable for extended release tablets.

Figure 4:
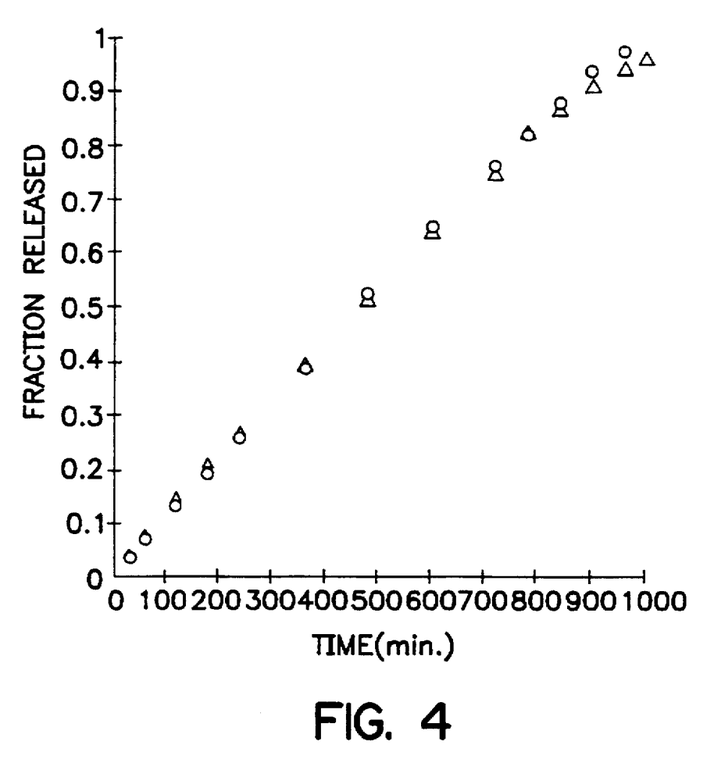
FIG. 4 is a graph showing the release of theophylline from the tablet of example 1 of the present invention in 0.1N HCl solution and phosphate buffer of pH 5.8.
Figure 6:
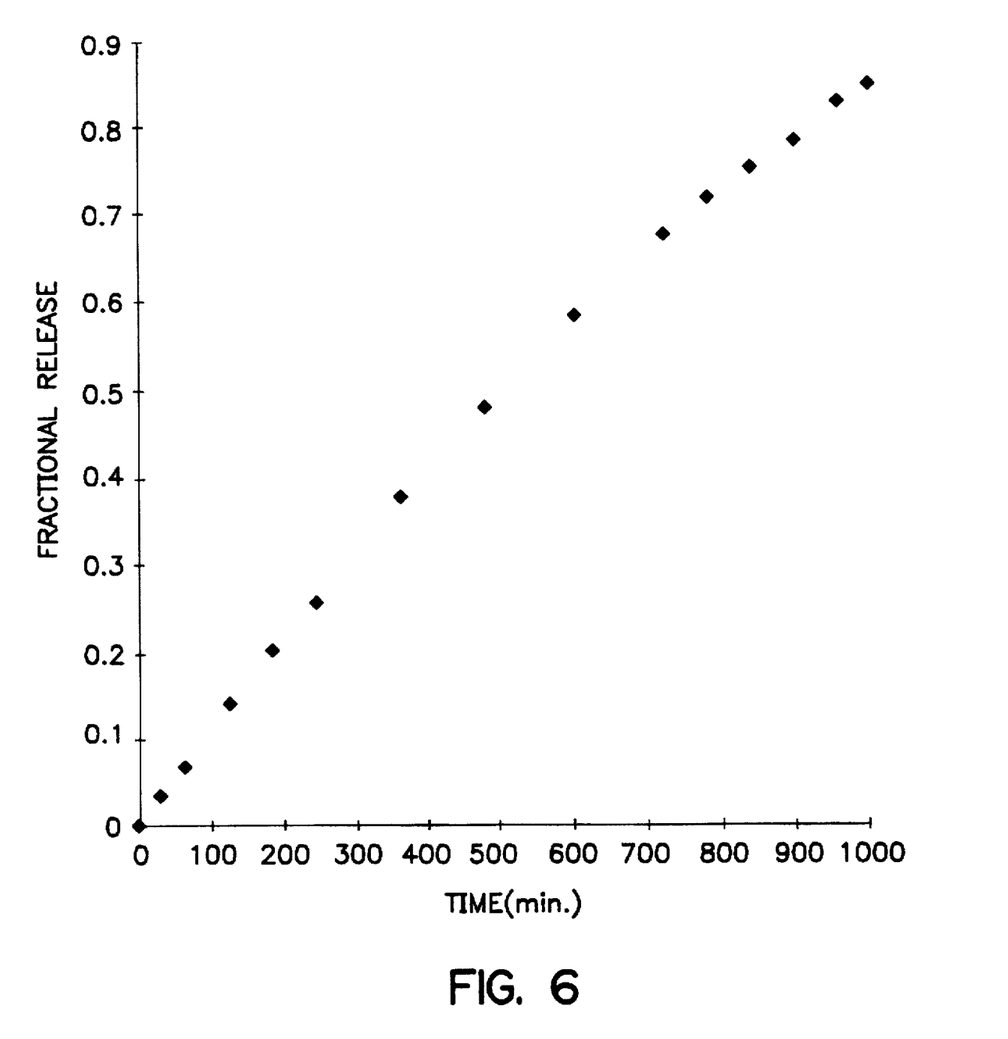
FIG. 6 is a graph showing the release of theophylline from the tablets of example 1 of the present invention when placed in deionized water.

Drug release in vitro should (ideally) be independent of variations in pH of the dissolution medium. If this were true, this would enable lead to a correlation between the in vitro studies and in vivo results. To measure drug release as a function of changes in dissolution media pH, dissolution studies were conducted using the tablets set forth in Table 2 above. The tablets were first introduced into 0.1N HCl solution for 60 minutes. The tablet was then transferred into phosphate buffer solution having a pH of 5.8. The release profile for the tablets in pH 5.8 phosphate buffer are shown in FIG. 4, along with the drug release profile for tablets maintained in 0.1N HCl solution. As can be seen from FIG. 4, the release profile for the phosphate buffer solution was nearly superimposed upon the release profile for 0.1N HCl solution. Further, drug release from the tablets of the present invention introduced into deionized water is shown in FIG. 6. The release of pharmaceutical agent in deionized water was nearly the same as in phosphate buffer and 0.1N HCl solution. This shows that drug release from the present invention is not significantly affected by changes in pH of the dissolution medium. This may be a result of the non-ionic property of polyethylene oxide.

One advantage of the tablets of the present invention, is their low density and their ability to trap generated gases within the polymeric matrix. Tablets having the composition set forth in Table 2 were introduced to dissolution medium (0.1N HCl solution). All tablets floated to the upper ⅓ portion of the dissolution vessel within about 15 minutes from their introduction into the dissolution medium. All tablets remained in that upper ⅓ portion until completely dissolved, indicating successful evolution of gas and buoyancy adjustment sufficient to prevent the passage of the tablet from the stomach to the small intestine.

Figure 5:
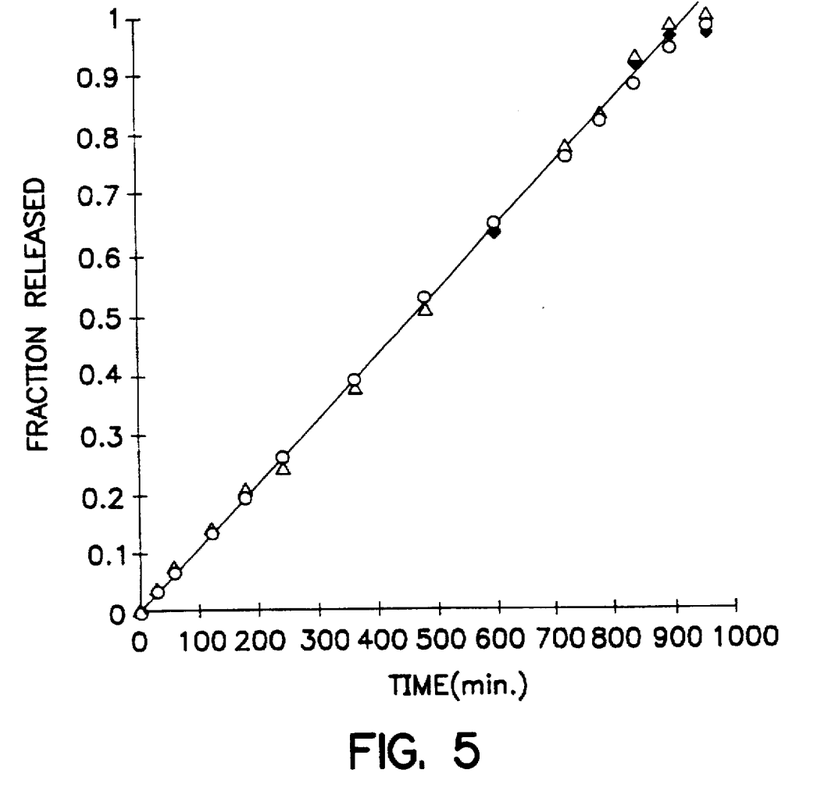
FIG. 5 is a graph showing the release of theophylline from tablets produced in accordance with example 1 of the present invention with various compaction forces.

The influence of compaction force on the release of theophylline from the tablets having compositions shown in Table 2 was evaluated. The tablets were compressed to 2500, 5000, and 7500 lb. As can be seen from FIG. 5, the compaction force did not significantly affect the release patterns to any significant degree. Insensitivity to compaction force is desirable, especially in a three layer tablet composition. Thus, during production, compaction force can be preset and wide variations can be tolerated without affecting the drug release properties of the tablet. This is very desirable from a production standpoint.

EXAMPLE 2

Figure 7:
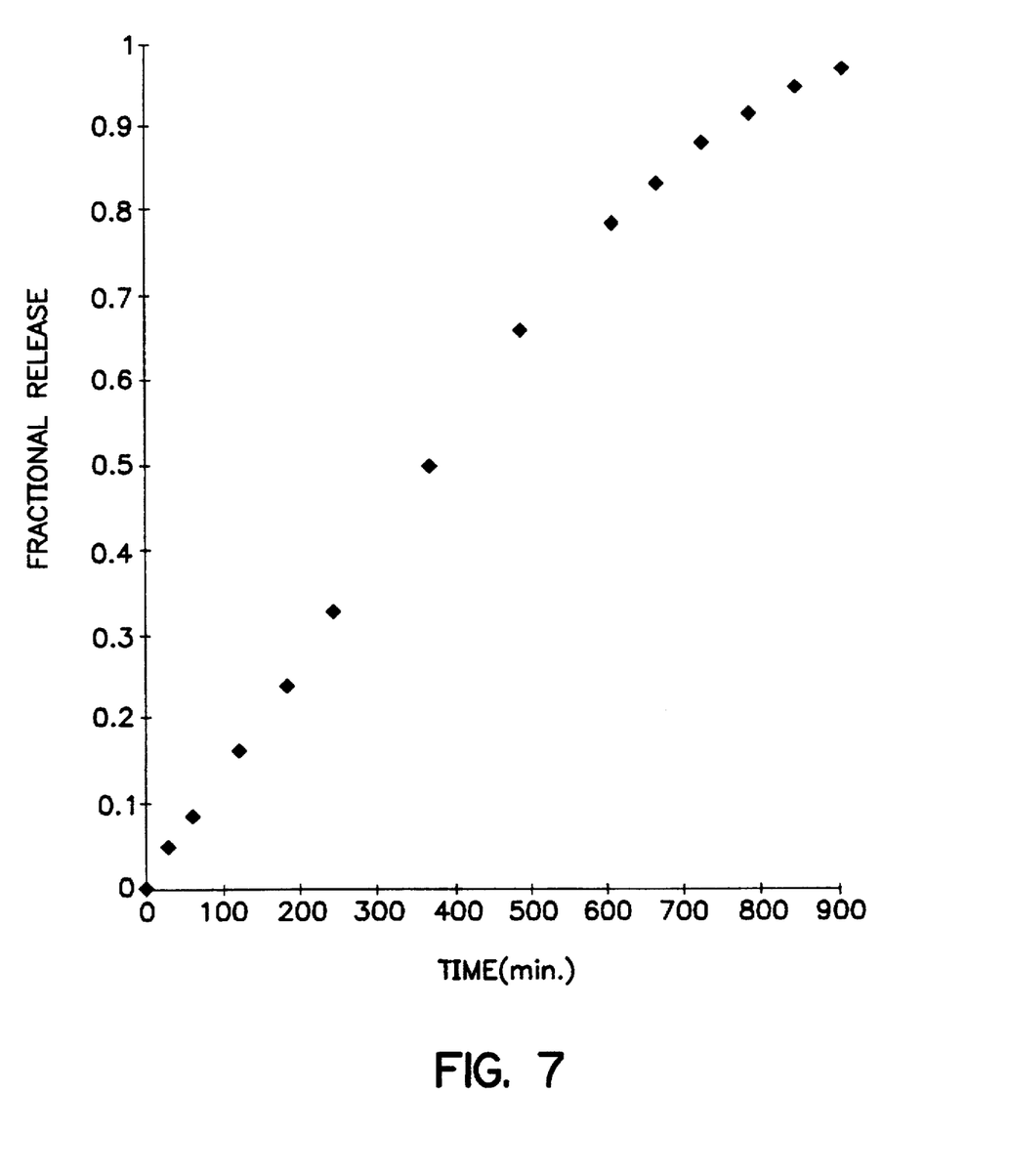
FIG. 7 is a graph showing the release of diltiazem from tablets produced in accordance with example 2 of the present invention when placed in 0.1N HCl solution.

Tablets were also prepared according to the composition shown in Table 2, but in this case, diltiazem was substituted for theophylline. In all other respects, this composition and the method for making the tablets is as set forth previously with respect to those tablets containing theophylline anhydrous. The tablets were tested the same way set forth above, and the release profile of diltiazem in 0.1N HCl solution is shown in FIG. 7. These results show that near zero-order release characteristics were also achieved using diltiazem instead of theophylline.

EXAMPLE 3

Tablets were prepared according to the method of Example 1 using various compositions as set forth below. All tablets included theophylline as a pharmaceutical agent. All tablets were tested by placing in 0.1N HCl solution over a 15 hour period. Tablets were prepared based on variations to the basic composition shown in Table 3 below. The total thickness of each tablet was 4 mm. In each case, 1% magnesium stearate was added to each layer as a lubricant. Within the ranges shown, the formulations were optimized for the required compressibility and release rate. All barrier layers had a weight of 200 mg.

TABLE 3

Formulation Components of
Asymmetric Configuration Drug Delivery System

| Layer | Components | % (W/W) |
|---|---|---|
| 4 | Polyethylene Oxide/HPMC | ~50–60 |
|   | Sodium Bicarbonate | ~10 |
|   | Lactose | ~30–40 |
| 5 | Polyethylene Oxide/HPMC | ~50 |
|   | Theophylline Anhydrous | ~34 |
|   | Lactose | ~16 |
| 2 | Polyethylene Oxide/HPMC | ~50 |
|   | Lactose | ~50 |

Figure 8:
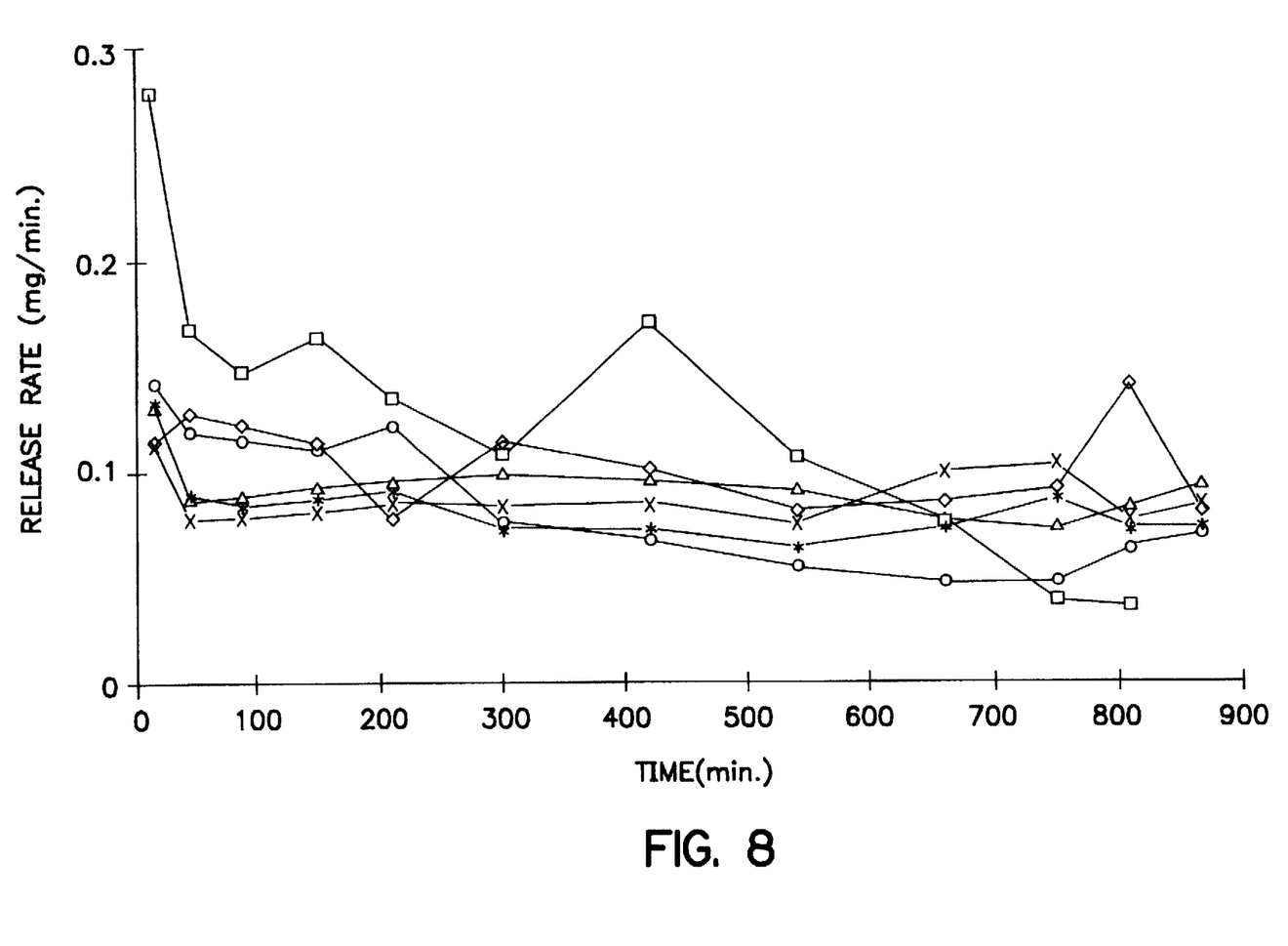
FIG. 8 is a graph showing the release profile of theophylline from tablets produced in accordance with example 3 of the present invention.
Figure 9:
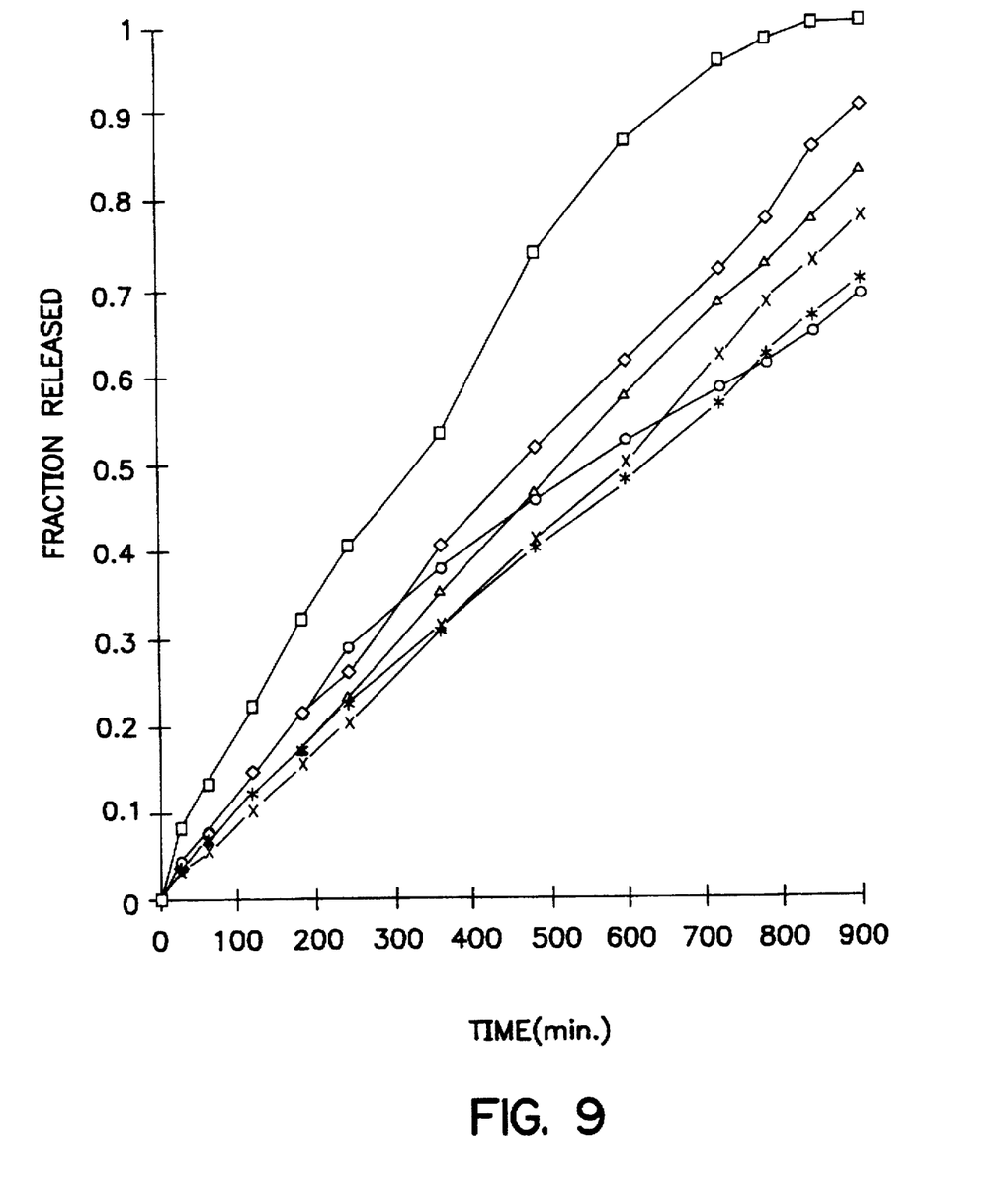
FIG. 9 is a graph showing the rate of release of theophylline from tablets produced in accordance with example 3 of the present invention.

Tablets were prepared where both barrier layers (2 and 4) had a composition of 85% ethyl cellulose and 15% HPMC. Results for these tablets are shown in FIGS. 8 and 9 marked with a circle (O). Tablets were prepared with one barrier layer (2) having a composition of 85% ethyl cellulose and 15% HPMC, and the other barrier layer having the composition of layer 4 in Table 3. Results for these tablets are shown in FIGS. 8 and 9 marked with a cross (X). Tablets were prepared with one barrier layer (2) having a composition of 85% ethyl cellulose and 15% HPMC and the other barrier layer having a composition of 50% lactose and 50% PEO having a molecular weight of $1 \times 10^6$. Results for these tablets are shown in FIGS. 8 and 9 marked with a diamond (◊). Tablets were prepared with one barrier layer (2) having a composition of 85% ethyl cellulose and 15% HPMC and the other barrier layer having a composition of 75% lactose and 25% PEO having a molecular weight of $1 \times 10^6$. Results for these tablets are shown in FIGS. 8 and 9 marked with a triangle (Δ). Tablets were prepared with one barrier layer (2) having a composition of 85% ethyl cellulose and 15% HPMC and the other barrier layer having a composition of 100% PEO having a molecular weight of $1 \times 10^6$. Results for these tablets are shown in FIGS. 8 and 9 marked with an asterisk (*). Tablets were prepared with no barrier layers. The entire tablet had the composition shown for layer 5. Results for these tablets are shown in FIGS. 8 and 9 marked with a box (□).

As can be seen from FIGS. 8 and 9, while the rate of release from the tablets varied with the composition, the release rate was nearly constant for all compositions within the scope of the invention. The exceptions were the control tablets having no barrier layers (marked with a box (□)). This shows the versatility of the present invention.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A controlled release pharmaceutical tablet comprising:
   a first barrier layer comprising a first swellable, erodible polymer;
   a drug layer comprising a second swellable, erodible polymer; and
   a second barrier layer comprising a third swellable, erodible polymer, wherein
   said first and second barrier layers are adapted to swell and to erode faster than said drug layer;
   said faster swellability and erodibility of said first and third layers adapted to increase drug delivery from the onset of dissolution.

2. The tablet of claim 1 wherein said second swellable, erodible polymer comprises polyethylene oxide.

3. The tablet of claim 2 wherein said polyethylene oxide has an average molecular weight of between $1 \times 10^6$ and $2 \times 10^6$.

4. The tablet of claim 1 wherein the molecular weight of said second swellable, erodible polymer is greater than the molecular weight of said first and third swellable, erodible polymers.

5. The tablet of claim 4 wherein said first and second barrier layers and said drug layer each have a different thickness.

6. The tablet of claim 4 wherein said first, second, and third swellable, erodible polymers each have a different molecular weight.

7. The tablet of claim 4 wherein said barrier layers and said drug layer each include an erosion promoter, and wherein the proportion of erosion promoters in said barrier layers is greater than the proportion of erosion promoters in said drug layer.

8. The tablet of claim 4 wherein at least one of said barrier layers includes a pharmaceutical agent.

9. The tablet of claim 1 wherein at least one of said layers includes a gas-evolving material.

10. The tablet of claim 1 wherein at least one of said barrier layers includes a pharmaceutical agent.

11. The tablet of claim 10 wherein said pharmaceutical agent in said barrier layer is the same as said pharmaceutical agent in said drug layer.

12. The tablet of claim 1 wherein the thickness of said drug layer is greater than the thickness of either of said barrier layers.

13. The tablet of claim 12 wherein said first and second barrier layers and said drug layer each have a different thickness.

14. The tablet of claim 12 wherein said barrier layers and said drug layer each include an erosion promoter, and wherein the proportion of erosion promoters in said barrier layers is greater than the proportion of erosion promoters in said drug layer.

15. The tablet of claim 12 wherein at least one of said layers includes a gas-evolving material.

16. The tablet of claim 12 wherein at least one of said barrier layers includes a pharmaceutical agent.

17. The tablet of claim 1 wherein said barrier layers and said drug layer each include an erosion promoter, and wherein the proportion of erosion promoters in said barrier layers is greater than the proportion of erosion promoters in said drug layer.

18. The tablet of claim 17 wherein the thickness of said drug layer is greater than the thickness of either of said barrier layers.

19. The tablet of claim 18 wherein said first and second barrier layers and said drug layer each have a different thickness.

20. The tablet of claim 19 wherein at least one of said layers includes a gas-evolving material.

21. The tablet of claim 20 wherein at least one of said barrier layers includes a pharmaceutical agent.

22. The tablet of claim 17 wherein the molecular weight of said second swellable, erodible polymer is greater than the molecular weight of said first and third swellable, erodible polymers.

23. The tablet of claim 22 wherein said first, second, and third swellable, erodible polymers each have a different molecular weight.

24. The tablet of claim 17 wherein said second swellable, erodible polymer comprises polyethylene oxide.

25. The tablet of claim 24 wherein said polyethylene oxide has an average molecular weight of between $1\times10^6$ and $2\times10^6$.

26. An asymmetric controlled release pharmaceutical tablet comprising:

a first barrier layer having a first thickness comprising a first swellable, erodible polymer, said first barrier layer having a first rate of erosion;

a drug layer having a second thickness comprising a second swellable, erodible polymer, said drug layer having a second rate of erosion; and a second barrier layer having a third thickness comprising a third swellable, erodible polymer, said second barrier layer having a third rate of erosion, wherein said first, second, and third thicknesses are all different; and said first and third rates of erosion are both greater than said second rate of erosion; and said faster swellability and erodibility of said first and third layers adapted to increase drug delivery from the onset of dissolution.

27. A controlled release pharmaceutical tablet as recited in claim 1, where one of said first and third layers is adapted to be fully eroded prior to the other of said layers.

28. A controlled release pharmaceutical tablet, as recited in claim 27, wherein said first eroding layer is fully eroded within 2–4 hours of the onset of dissolution.

29. A controlled release pharmaceutical tablet, as recited in claim 28, wherein said second remaining barrier is adapted to be fully eroded when the drug remaining in the inner layer is on the order of 50–60% of the amount of drug in the inner layer originally.

* * * * *